US00PP17056P3

(12) United States Plant Patent
Redman

(10) Patent No.: US PP17,056 P3
(45) Date of Patent: Aug. 22, 2006

(54) *CHRYSANTHEMUM* PLANT NAMED 'MIDNIGHT TIME'

(50) Latin Name: *Chrysanthemum morifolium*
Varietal Denomination: Midnight Time

(75) Inventor: Ruth Redman, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 0 days.

(21) Appl. No.: 11/146,391

(22) Filed: Jun. 6, 2005

(65) Prior Publication Data

US 2005/0273897 P1 Dec. 8, 2005

Related U.S. Application Data

(60) Provisional application No. 60/578,008, filed on Jun. 7, 2004.

(51) Int. Cl.
*A01H 5/00* (2006.01)

(52) U.S. Cl. ..... Plt./287

(58) Field of Classification Search ..... Plt./287
See application file for complete search history.

(56) References Cited

U.S. PATENT DOCUMENTS

PP15,755 P2 5/2005 Redman ..... Plt./292

*Primary Examiner*—Kent Bell
*Assistant Examiner*—Annette H Para
(74) *Attorney, Agent, or Firm*—Winston & Strawn LLP

(57) ABSTRACT

A new variety of *Chrysanthemum* plant named 'Midnight Time', having a good uniform canopy of purple decorative flowers. The new variety has a uniform spreading habit with a good foliage presentation.

1 Drawing Sheet

Latin name of the genus and species: Botanical classification: *Chrysanthemum morifolium.*

Variety denomination: The new *Chrysanthemum* variety denomination is 'Midnight Time'.

BACKGROUND OF THE INVENTION

The present invention comprises a new and distinct cultivar of *chrysanthemum* botanically known as *Chrysanthemum morifolium,* and referred to by the variety name 'Midnight Time'.

'Midnight Time', identified as '22054-0', originated from a cross made in a controlled breeding program in Chichester, West Sussex, United Kingdom. The female of the new variety is '20302-0' (unpatented seedling) and the male parent is the variety known as 'Trumbull' (unpatented variety).

The new variety 'Midnight Time' has been asexually reproduced by vegetative cuttings in Chichester, West Sussex, United Kingdom, and the distinguishing characteristics are retained through successive generations of asexual reproduction.

BRIEF SUMMARY OF THE INVENTION

'Midnight Time' is a pot type of *Chrysanthemum* plant variety having purple decorative flowers.

Comparison With Female Parent

Plants of the new *Chrysanthemum* variety 'Midnight Time' are similar to the parent '20302-0' in plant habit and growth rate. In side-by-side comparisons in Chichester, West Sussex, United Kingdom, under commercial practice, plants of the new *chrysanthemum* variety 'Midnight Time' differed from plants of the parent '20302-0' in the following characteristics:

1. The new variety 'Midnight Time' produces purple decorative flowers whereas the parent '20302-0' produces white decorative flowers.
2. Plants of the new variety 'Midnight Time' have smaller and shorter inflorescence than plants of '20302-0'.

Comparison With Male Parent

Plants of the new *Chrysanthemum* variety 'Midnight Time' are similar to the parent 'Trumbull' in plant habit and growth rate. In side-by-side comparisons in Chichester, West Sussex, United Kingdom, under commercial practice, plants of the new *chrysanthemum* variety 'Midnight Time' differed from plants of the parent 'Trumbull' in the following characteristics:

1. The new variety 'Midnight Time' produces purple decorative flowers whereas the parent 'Trumbull' produces red single flowers.
2. Plants of the new variety 'Midnight Time' have smaller and shorter inflorescence than plants of 'Trumbull'.

Comparison with 'Vamp Time Dark Pink'

Plants of the new *Chrysanthemum* variety 'Midnight Time' are similar to the variety 'Vamp Time Dark Pink' (U.S. Plant Pat. No. 15,755) in plant habit and growth rate. However, in side-by-side comparisons in Chichester, West Sussex, United Kingdom, under commercial practice, plants of the new *Chrysanthemum* variety 'Midnight Time' differed from plants of the variety 'Vamp Time Dark Pink' in the following characteristics:

1. The new variety 'Midnight Time' produces purple decorative flowers whereas 'Vamp Time Dark Pink' produces dark pink decorative flowers.

2. Plants of the new variety 'Midnight Time' have smaller and shorter inflorescence than plants of 'Vamp Time Dark Pink'.
3. Plants of the new variety 'Midnight Time' have a quicker response when compared to plants of 'Vamp Time Dark Pink'.

BRIEF DESCRIPTION OF ILLUSTRATIONS

Typical specimens of the plant and flowers for the new *Chrysanthemum* variety 'Midnight Time' are shown in the accompanying digital photograph. The colors shown are as true as possible within the usual limits of this kind of illustration.

FIG. 1 is a whole plant view of the new variety 'Midnight Time' grown in a pot.

The plant shown in the illustration is 54 days from the commencement of Short Days.

DETAILED BOTANICAL DESCRIPTION

The following description of the new *Chrysanthemum* variety 'Midnight Time' is of plants grown in a greenhouse in Chichester, West Sussex, United Kingdom, in the month of September. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5,000 to 6,000 foot candles. The plants respond well to the use of growth retardant, such as one B9 treatment at about 2 gram per liter. To produce a commercial product the plants may be pinched once with the center bud removed. The typical container size for commercial growth is 1 liter. It has been observed that the shelf life of the new variety is about 21 days with a response time of about 7 weeks. The new variety is suitable for growth in a temperature range of 15° C. to 25° C.

The following description is with respect to a plant produced as pot. In the description of this new *Chrysanthemum* variety, color values have been taken from The Royal Horticultural Society Colour Chart (R.H.S.C.C.).

Plant

Plant type: Pot.
Habit: Upright and free branching.
Height (cm): 22.
Width (cm): 32.
Stem:
- *Length* (*cm*).—6.
- *Diameter* (*cm*).—0.8.
- *Texture.*—Slightly pubescent.
- *Color.*—137D.

Branching characteristics: Upright and free branching.
Lateral branches:
- *Length* (*cm*).—12.
- *Diameter* (*cm*).—0.5.
- *Texture.*—Slightly pubescent.

Number of breaks from pinch: 5.
Response time: 50 days.
Vigor: medium to tall.
Shelf life: 21 days.
Life of blooms: 21 days.
Disease (susceptibility/resistance observed): None observed to date.
Pest (susceptibility/resistance observed): None observed to date.
Drought and temperature (susceptibility/resistance observed): None observed to date.
Growth retardant type and treatment: 3 applications of 2.5 gm/liter B9 @ 2, 21 and 28 days after sticking unrooted cuttings.

The plants were grown for 2 weeks in Long Day conditions (20 hours of light) and then transferred to Short Day conditions (13 hours of dark).

Propagation:
- *Type.*—Vegetative propagation via stem cuttings.
- *Time to rooting.*—14 days with soil temperatures of 18° C.
- *Rooting habit.*—After 7 days the first roots emerge and form root primordia. In 14 Long Days a complete root system is developed.

Foliage

Number of leaves per lateral branch: 12.
Compound or single: Single.
Arrangement of leaves: Alternate.
- *Shape of leaf.*—Lobed.
- *Size of leaf.*—Width (cm): 3; Length (cm): 6.
- *Leaf apex.*—Acute.
- *Base.*—Cordate.
- *Attachment.*—Petioled.
- *Aspect.*—Slightly undulating.
- *Margin.*—Entire.
- *Surface characteristics.*—Top: slightly pubescent. Bottom: pubescent.

Petiole:
- *Color.*—138C.
- *Length* (*cm*).—1.5.
- *Diameter* (*cm*).—0.3.

Venation: Color: Upper side: 138B. Under side: 138C.
Color:
- *Mature leaf, upper side.*—138A; under side: 138B.
- *Young leaf, upper side.*—137B; under side: 138B.

Flower

Flower appearance: Matte.
Flower type: Decorative.
Flower form: Incurving.
Flower shape: Circular.
Flowering habit: Cyme.
Number of blossoms per branch: 5.
Typical and observed flowering season: January to December.
Inflorescence form:
- *Depth of fully expanded blossoms* (*cm*).—1.5.
- *Diameter of fully expanded blossoms* (*cm*).—6.

Phyllaries:
- *Number.*—25.
- *Color.*—138B.
- *Length* (*cm*).—0.8.
- *Width* (*cm*).—0.2.
- *Texture/appearance.*—Pubescent.

Peduncle:
- *Length* (*cm*).—12.
- *Diameter* (*cm*).—0.5.

*Angle from stem* (*degrees*).—20.
*Color.*—137D.
*Surface.*—Slightly pubescent.
*Habit.*—Slightly undulating.
*Strength.*—Strong.

Pedicel:
*Length.*—Terminal (cm): 2; lateral (cm): 1.2.
*Diameter* (*cm*).—0.3.
*Color.*—137D.
*Surface.*—Slightly pubescent.
*Habit.*—Slightly undulating.
*Strength.*—Moderately strong.

Ray florets:
*Form/shape.*—Straight with parallel edges.
*Texture/appearance.*—Matte.
*Number per flower.*—>150.
*Length* (*cm*).—2.5; Width (cm): 0.5.
*Apex.*—Dentate.
*Base.*—Tapered.
*Margin.*—Entire.

Disc florets:
*Form/shape.*—Cylindric.
*Texture/appearance.*—Shiny.
*Number per flower.*—10.
*Length* (*cm*).—0.5; Width (cm): 0.1.
*Diameter of disc* (*cm*).—0.4.

Fragrance: None.

Flower bud (at onset of color):
*Length* (*cm*).—0.6.
*Diameter* (*cm*).—0.7.
*Form/shape.*—Globular.

General flower color:
1. *Ray florets, upper side.*—Immature: 61A. Mature: 61B. Older/Fading: 63A.
2. *Ray florets, under side.*—Immature: 63A. Mature: 63B. Older/Fading: 63C.
3. *Bud.*—63A.

Flower progression with age: The flower form does not change but there is a slight color fading with age.

Reproductive Organs

Gynoecium present on Ray and Disc florets.

Ray florets per individual flower: Pistillate.
*Pistil number.*—>150.
*Stigma color.*—154A.
*Stigma shape.*—Forked.
*Style color.*—154B.
*Style length* (*cm*).—0.3.

Disc florets per individual flower: Pistillate.
*Pistil number.*—10.
*Stigma color.*—154A.
*Stigma shape.*—Forked.
*Style color.*—154B.
*Style length* (*cm*).—0.4.

Androecium: None observed.

Fruit and seeds: None observed to date.

What is claimed is:

1. A new and distinct variety of *Chyrsanthemum* plant, substantially as described and illustrated herein.

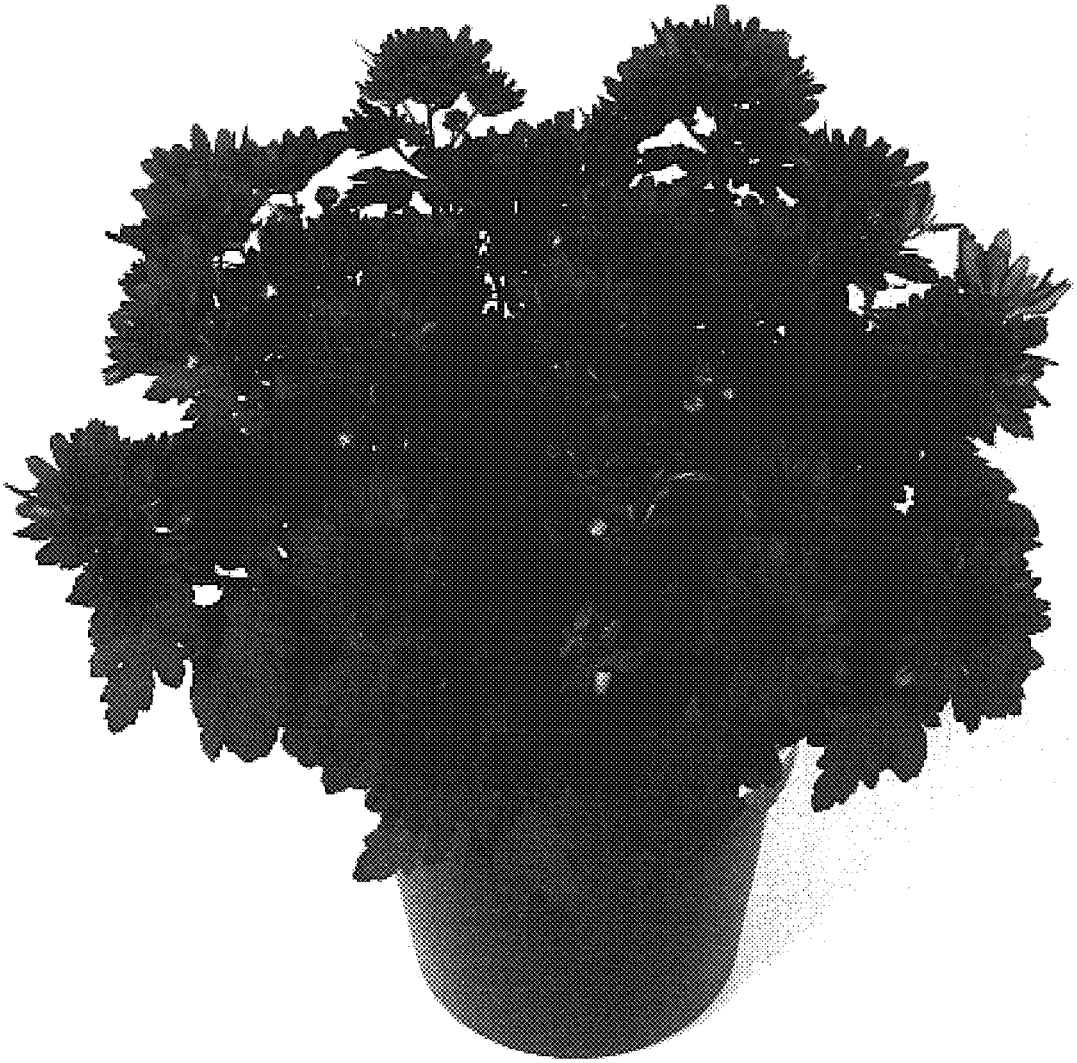

* * * * *